United States Patent [19]

Reist et al.

[11] Patent Number: 5,047,533

[45] Date of Patent: Sep. 10, 1991

[54] ACYCLIC PURINE PHOSPHONATE NUCLEOTIDE ANALOGS

[75] Inventors: Elmer J. Reist, Menlo Park; Priscilla A. Sturm, Mountain View, both of Calif.

[73] Assignee: SRI International, Menlo Park, Calif.

[21] Appl. No.: 469,791

[22] Filed: Jan. 22, 1990

Related U.S. Application Data

[63] Continuation of Ser. No. 5,471, Jan. 20, 1987, abandoned, which is a continuation-in-part of Ser. No. 828,231, Feb. 10, 1986, abandoned, which is a continuation-in-part of Ser. No. 497,720, May 24, 1983, abandoned.

[51] Int. Cl.$^5$ .................. A61K 31/675; C07F 9/6561
[52] U.S. Cl. .................................... 544/244; 558/183; 544/276
[58] Field of Search ........................... 544/244; 514/81

[56] References Cited

U.S. PATENT DOCUMENTS

| 3,238,191 | 3/1966 | Myers et al. | 536/27 |
|---|---|---|---|
| 3,446,793 | 5/1969 | Jones et al. | 536/27 |
| 3,524,846 | 8/1970 | Moffatt et al. | 536/28 |
| 3,560,478 | 2/1971 | Myers et al. | 536/27 |
| 3,662,031 | 5/1972 | Moffatt et al. | 536/29 X |
| 4,287,188 | 9/1981 | Schaeffer | 514/81 |
| 4,355,032 | 10/1982 | Verheyden et al. | 544/276 X |
| 4,360,522 | 11/1982 | Schaeffer | 544/244 X |
| 4,565,868 | 1/1986 | Verheyden et al. | 544/276 |
| 4,724,233 | 2/1988 | DeClercq et al. | 514/81 |
| 4,755,516 | 7/1988 | Tolman et al. | 514/262 |
| 4,808,716 | 2/1989 | Holy et al. | 544/244 |

FOREIGN PATENT DOCUMENTS

| 0015584 | 3/1980 | European Pat. Off. . |
|---|---|---|
| 0049072 | 4/1982 | European Pat. Off. . |
| 0055239 | 6/1982 | European Pat. Off. . |
| 0074306 | 3/1983 | European Pat. Off. . |
| 0173624 | 3/1986 | European Pat. Off. . |
| 2009834 | 9/1970 | Fed. Rep. of Germany . |
| 3045342 | 7/1982 | Fed. Rep. of Germany . |
| 3045375 | 7/1982 | Fed. Rep. of Germany . |
| 3534774 | 4/1987 | Fed. Rep. of Germany ...... 544/244 |
| 2381781 | 2/1978 | France . |
| PCT/US84/-00737 | 12/1984 | PCT Int'l Appl. . |
| 1243214 | 8/1971 | United Kingdom . |
| 1243213 | 5/1972 | United Kingdom . |

OTHER PUBLICATIONS

Jones et al., J Am Chem Soc (Sep. 11, 1968), 90.19:5337-38.
Jones et al., J. Am Chem Soc (Sep. 9, 1970) 92.18:5510-11.
Hampton et al., J Am Chem Soc (Jun. 27 1973) 95.13:4404-14.
Hampton et al., Biochemistry (1973), 12.9:1730-36.
Montgomery et al., Journal of Heterocyclic Chemistry (1974), XI:211-18.
Engel, Chemical Reviews (1977), 77:349-67.
Carrasco, Nature (Apr. 20, 1978), pp. 694-699.
Montgomery et al., J of Medicinal Chem (1979), 22.1:109-11.
Hirano et al., Acta Virol (1979), 23:266-30.
St. Clair et al., Antimicrobial Agents and Chemotherapy (1980), 18:741-45.
Bauer, Developments in Antiviral Therapy (1980), pp. 43-51.
Kelley et al., J Med Chem (1981), 24:1528-31.
Derse et al., Chem Abstracts (1981), 95:217005b.
Field et al., Journal of Infectious Diseases (Feb. 1981), 143:281-85.
Allaudeen et al., Chem Abstracts (1982), 97:141598r.
Acyclovir Symposium, The American Journal of Medicine (Jul. 20, 1982), 23.1A.
Hollmann et al., Liebigs Ann Chem (1984), pp. 98-107.
Prisbe et al., J Med Chem (1986), 29:671-75.
Streicher et al., Chemica Scripta (1986), 26:179-83.
Duke et al., Antiviral Research (1986), 6:299-308.

Primary Examiner—Diana Rivers
Attorney, Agent, or Firm—Irell & Manella

[57] ABSTRACT

Certain open chain purine nucleoside phosphonate derivatives have antiviral activity against the Herpes group of viruses, and also show effective antiviral activity against retroviruses, including human immunodeficiency virus (HIV). These compounds have the formula

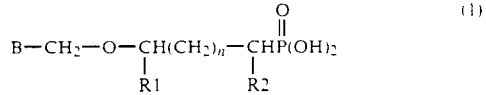

wherein B represents a substituted or unsubstituted purine base, especially adenine or guanine and their halogenated derivatives. R1 is selected from H, methyl, hydroxymethyl, halomethyl, azidomethyl, and cyano; R2 is selected from H, methyl, hydroxymethyl, halomethyl, azidomethyl, cyano, and OH; also when R2 is OH the carbon to which it is attached may be oxidized so that the H there shown and R2 together may be =O; and n is an integer of 0-5. The compounds of the invention further include the pharmaceutically acceptable mono and dibasic salts and the mono- and diesters of the phosphonate moiety and the acid addition salts of the murine-substituted purines. In addition, when R1 or R2 is —CH$_2$OH, or when R2 is OH, the acyl (1-6C) esters of these alcohols are included in the invention. Further, when n is 0, 1, or 2 and R1 is CH$_2$OH, the compounds of Formula 1 include the cyclic forms wherein formal dehydration between R1 and one of the —OH groups on the phosphonate results in compounds of the formula:

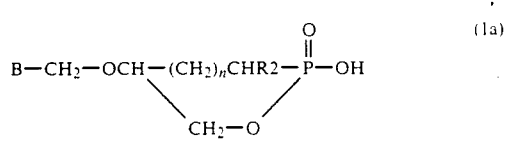

and their corresponding salts and esters.

5 Claims, No Drawings

ACYCLIC PURINE PHOSPHONATE NUCLEOTIDE ANALOGS

This is a continuation of U.S. patent application Ser. No. 07/005,471, filed Jan. 20, 1987, which was a continuation-in-part of U.S. Ser. No. 06/828,231, filed Feb. 10, 1986, which was in turn a continuation-in-part of U.S. Ser. No. 06/497,720, filed May 24, 1983, all of which are all now abandoned.

FIELD OF THE INVENTION

The invention relates to nucleotide analogs which are antiviral agents. Specifically, it relates to acyclic purine phosphonate nucleotide analogs which are effective against both herpes-type virus and against RNA retroviruses such as HTLV-III (HIV).

BACKGROUND OF THE INVENTION

There are five known herpes-type viruses which affect human beings: herpes zoster (chicken pox), herpes simplex virus I & II (cold sores and genital herpes), cytomegalovirus (cytomegalic inclusion disease), and Epstein-Barr virus (mononucleosis). The herpes viruses are medium-sized viruses containing double-stranded DNA. The nucleocapsid is about 100 nm in diameter and is surrounded by a lipid containing envelope. The virion is 150-200 nm in diameter, and permits latent infections which last for the life span of the host even when antibodies are present.

A very different group of virus particles is the RNA virus group. Of particular interest within this group are the retroviruses which include most tumor virions, including human T-cell leukemia virus (HTLV III), now designated human immunodeficiency virus (HIV). HIV or its close relatives are believed to be the cause of Acquired Immune Deficiency Syndrome (AIDS).

General antiviral agents are numerous. Several nucleoside analogs, such as iododeoxyuridine and 5-E-bromovinyldeoxyuridine, are believed to act only after conversion by viral thymidine kinase (but not by host TK) to the nucleotide form, which is then converted to the triphosphate and incorporated into the viral DNA, thus inhibiting its replication. These analogs are ineffective in certain herpes strains which are TK$^-$, and even TK$^+$ strains resistant to certain specific members of this class of agents have been reported (Field, H., et al, *J Infect Disease* (1981) 143:281; Hirano, A., et al, *Acta Virol* (1979) 23:226). It would not be expected that agents which work by this mechanism would be effective against RNA viruses.

The antiviral agents of the present invention are acyclic nucleotide analogs which are phosphonates rather than phosphates. A large number of phosphonate analogs of nucleotides are described by Engel, R., *Chem Reviews* (1977) 11: (3) 349-367. Phosphonate compounds which are direct cyclic nucleotide analogs are also disclosed in U.S. Pat. No. 3,560,478; German Patent Application No. DE 3,045,375VA1, published July 1, 1982; U.S. Pat. No. 3,446,793; British Patent No. 1,243,213; German Patent Application No. 2,009,834 published Sept. 17, 1970 and in Holman, J., et al, *Liebigs Annalen Chem* (1984) 98-107; Hampton, A., et al, *Biochemistry* (1973) 12:1730-1736; Jones, G. H., et al, *J Am Chem Soc* (1968) 90:5337-5338; Montgomery, J. A., et al, *J Med Chem* (1979) 22:109-111 and British Patent No. 1,243,214. In general, in the foregoing disclosures, the utility of the phosphonates is believed to reside in their structure being analogous to that of the nucleotides combined with enhanced stability due to the phosphonate moiety. In general, it is suggested that they are useful for whatever pharmacological purposes the corresponding nucleotides would serve.

For example, Montgomery, J., et al. *J Med Chem* (supra), suggest that the phosphonate analogs may be useful as cytotoxic agents analogous to the commonly used chemotherapeutic drug 5-fluorouracil by virtue of a similar ability to inhibit the essential enzyme thymidilate synthetase, essential for DNA synthesis. This enzyme is inhibited actually by the anabolic product of 5-fluorouracil, the corresponding monophosphate.

All of the foregoing referenced compounds retain the furanose cyclic structure of the ribose or deoxyribose. Nucleoside analogs in which the cyclic furanose structure is replaced by an open chain are well known antiviral agents. French Patent Application Publication No. 2,381,781 discloses these acyclic purine nucleosides and nucleotides; similar compounds are disclosed in EPO Application Publication Nos. 0049072 and 0074306. Antiviral activity of some of these compounds with regard to herpes simplex virus is confirmed, for example, by Kelley, J. L., et al, *J Med Chem* (1981) 34:1528-1531.

St. Clair, M. H., et al, *Antimicrob Agents Chemother* (1980) 18:741-745, as reported in Chem Abstracts (1981) 94:26701v, reported that virus strains sensitive to acyclovir (9-(2-hydroxyethoxymethyl) guanine) induced production of DNA polymerases which were sensitive to its triphosphate. The same group, in a report by Bauer, D. J., et al, *Dev Antiviral Therapy* (1980) 43:51, as reported in Chem Abstracts (1981) 94:167716r disclose that acyclovir is effective in vitro against Varicella-Zoster, Epstein-Barr virus, cytomegalovirus, and "B" virus, and postulate that it provides its antiviral activity by being a substrate for phosphorylation by a viral thymidine kinase, such as that specified by the herpes virus, and, in the resulting triphosphate form, inhibits herpes virus DNA polymerase.

It has now been found that a series of phosphonates containing open chain ethers in lieu of ribose or deoxyribose residues in analogs of purine nucleosides are effective as cytotoxic agents, both against herpes-type DNA virus, for example, cytomegalovirus, and against RNA virus, for example, HIV. While these analogs appear similar to acyclovir in general chemical structure, they actually are not, since the phosphonate compounds are markedly different from the nonphosphorylated acyclovir. It is also clear that the mechanism of action for the compounds of the invention in preventing proliferation of viral infection cannot be the same as that for acyclovir, since phosphorylation by viral thymidine kinase cannot occur.

After the date of the disclosure herein, publications have appeared disclosing anti-herpes activity of 9-(3-phosphono-1-propoxymethyl) guanine (EPO Publication No. 0173,624, published May 3, 1986) and 9-(3-phosphono-1-hydroxymethyl-1-propoxymethyl) guanine (Duke, A. E., et al., *Antiviral Res* (1986) 6:299-308; Prisbe, E. J., et al., *J Med Chem* (1986) 29:671-675).

DISCLOSURE OF THE INVENTION

The invention provides a class of open chain alkoxymethyl nucleoside analog phosphonates which are potent antiviral agents against both herpes-type, such as cytomegalovirus, and RNA retrovirus type infections.

These compounds are apparently able to penetrate the infected cell and successfully inactivate the virus.

Accordingly, in one aspect, the invention is directed to compounds of the formula:

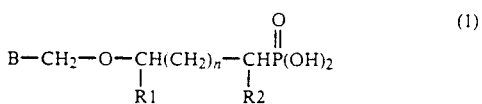

wherein B represents a substituted or unsubstituted purine base, especially adenine or guanine and their halogenated derivatives, R1 is selected from H, methyl, hydroxymethyl, halomethyl, azidomethyl, and cyano; R2 is selected from H, methyl, hydroxymethyl, halomethyl, azidomethyl, cyano, and OH; also when R2 is OH the carbon to which it is attached may be oxidized so that the H there shown and R2 together may be =O; and n is an integer of 0-5. The compounds of the invention further include the pharmaceutically acceptable mono- and dibasic salts and the mono- and diesters of the phosphonate moiety and the acid addition salts of the amino-substituted purines. In addition, when R1 or R2 is —CH$_2$OH, or when R2 is OH, the acyl (1-6 C) esters of these alcohols are included in the invention.

Further, when n is 0, 1, or 2 and R1 is CH$_2$OH, the compounds of Formula 1 include the cyclic forms wherein formal dehydration between R1 and one of the —OH groups on the phosphonate results in compounds of the formula:

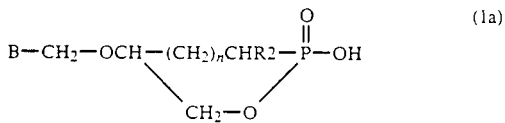

and their corresponding salts and esters.

In other aspects, the invention relates to pharmaceutical compositions containing the compounds of Formula 1 or 1a and to methods of treating or preventing herpes-type and RNA retrovirus infections by use of the compounds of Formula 1 (or 1a) or these compositions.

MODES OF CARRYING OUT THE INVENTION

A. Description of the Compounds of the Invention

The compounds of the invention may be in the form of phosphonic acids, esters, or pharmaceutically acceptable salts. In addition, the compounds may be used as the acid addition salts of the purine base.

The salts of the phosphonic acid moiety are salts with inorganic or organic bases and may be the mono- or dibasic salts. Salts derived from inorganic bases include the sodium, potassium, lithium, alkaline metal, such as magnesium and calcium salts, and salts of the transition metals or of aluminum. Salts derived from ammonium, potassium, sodium, calcium and magnesium are preferred. Suitable organic bases which are nontoxic and are capable of forming salts with the phosphonic acid moiety include various amines such as ethanolamine, triethylamine, isopropylamine, and amino acids such as lysine and arginine.

The phosphonic acid moiety of the compounds of the invention may also be in the form of the mono- or diester. The esters will be formed from alkyl, aryl-alkyl, and aryl alcohols containing 1-8 C. Alkyl alcohols include saturated or unsaturated straight chain, branch chain, or cyclic hydrocarbyl alcohols which may be substituted with one or two additional hydroxyl substituents or contain heterocyclic rings which include N, O and/or S atoms. Such moieties include, for example, methyl, isobutyl, n-octyl, 2-butenyl, 4-hydroxy-n-pentyl and so forth. When the alcohol is aryl or aryl-alkyl, the ester contains a phenyl substituent optionally substituted by one or two halo, alkoxy or hydroxy residues and representative groups of this class include the phenyl ester, the 3-hydroxyphenyl ester, the benzyl ester, and the 2-phenylethyl ester. Especially preferred are the alkyl (1-6 C) esters.

Since the purine substituents represented by B are basic, the compounds of the invention may also be supplied as the acid addition salts which retain the biological effectiveness and properties of the free bases and which are not otherwise undesirable. These salts may be formed from inorganic acids such as hydrochloric, hydrobromic acid or sulfuric acid, or from organic acids such as acetic, propionic, glycolic, oxalic, malonic, succinic, tartaric, cinnamic, methane sulfonic, p-toluene sulfonic, salicyclic, and so forth.

R1 is selected from hydrogen, methyl, substituted methyl and cyano. Substituted methyl groups include CH$_2$OH, CH$_2$N$_3$, CH$_2$Cl, CH$_2$Br, CH$_2$F, and CH$_2$I. R2 is selected from this same group, but can, in addition, be OH; or when OH, can be in oxidized form so that R2 in combination with H attached to the same C become =O. Further, when R2 or R1 is CH$_2$OH, or R2 is OH, the acyl esters (1-6 C), such as the esters of acetic, proprionic, butyric, and hexanoic acids, are also included.

The purine moieties of the invention are derived either from adenine or guanine each of which has a nucleus of the formula:

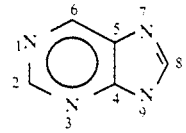

which has the numbering system shown. The numbering system will be retained herein as shown, regardless of substituents to the ring system. The bond at position 9 conjugates the acyclic or cyclic sugar derived moiety; further substitutions can be made at positions 2, 6 and 8.

For guanine the substituent at position 6 is hydroxyl (in the tautomer shown) and in adenine, —NH$_2$. Guanine has —NH$_2$ at position 2, adenine is unsubstituted. These and their further substituted analogs are preferred embodiments of the compounds of the invention. In addition, guanine or adenine analogs having halo groups in place of the hydroxyl or amino at position 6, such as chloro or bromo in particular, are preferred. In general suitable substituents at positions 2, 6 and 8 include hydroxyl, amino and halo wherein halo is defined as fluoro, chloro, bromo, and iodo.

Preferred values for n in the compound of Formula 1 are 0-2.

Representative embodiments of the compounds of the invention include:

9(3'-diethylphosphono-1'-propyloxymethyl)guanine;
9(3'-diethylphosphono-1'-propyloxymethyl)adenine;
9(3'-di-i-propylphosphono-1'-propyloxymethyl)adenine;
9(3'-di-i-propylphosphono-1'-propyloxymethyl)guanine;

9(3'-i-propylphosphono-1'-propyloxymethyl)guanine;
9(3'-dibutylphosphono-1'-n-butyloxymethyl)guanine;
6-chloro-9(4'-dibutylphosphono-1'-n-butyloxymethyl)guanine;
6-chloro-9(4'-dibutylphosphono-1'-n-butyloxymethyl)adenine;
6-chloro-9(5'-phosphono-1'-n-pentyloxymethyl-1'-choromethyl)guanine;
6-chloro-9(5'-phosphono-1'-n-pentyloxymethyl-1'-chloromethyl)adenine;
6-chloro-9(5'-phosphono-1'-n-pentyloxymethyl)adenine;
6-chloro-9(4'-phosphono-1'-n-pentyloxymethyl)adenine;
6-chloro-9(4'-phosphono-1'-n-pentyloxymethyl)guanine;
9(6'-phosphono-1'-n-hexyloxmethyl-1'-hydroxymethyl)guanine;
8-bromo-9(6'-phosphono-1'-n-hexyloxymethyl-1'-hydroxymethyl)guanine;
8-chloro-9(6'-phosphono-1'-n-hexyloxymethyl-1'-hydroxymethyl)guanine;
9(6'-phosphono-1'-n-hexyloxymethyl-1'-hydroxymethyl)adenine;
8-chloro-9(6'-phosphono-1'-n-hexyloxymethyl-1'-hydroxymethyl)adenine;
8-bromo-9(6'-phosphono-1'-n-hexyloxymethyl-1'-hydroxymethyl)adenine;
6-chloro-9(6'-phosphono-1'-n-hexyloxymethyl-1'-hydroxymethyl)adenine;
6-chloro-9(6'-phosphono-1'-n-hexyloxymethyl-6'-keto)guanine;
6-chloro-9(4'-phosphono-1'-n-pentyloxymethyl-1'-hydroxymethyl)guanine;
6-chloro-9(5'-phosphono-1'-n-pentyloxymethyl-5'-keto)adenine; and
6-chloro-9(4'-phosphono-1'-n-butyloxymethyl-4'-keto)adenine;
and their various esters and salts as set forth above.

B. Preparation of the Invention Compounds

Reaction Scheme 1 shows the general method to prepare the compounds of Formula 1.

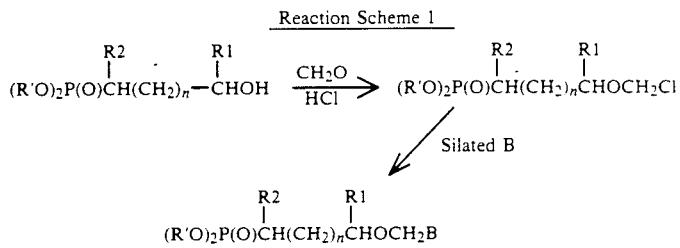

As shown in Reaction Scheme 1, treatment of the intermediate alcohol, $(R'O)_2P(O)CH(R2)(CH_2)_nCH(R1)OH$, with formaldehyde in the presence of hydrochloric acid provides the corresponding chloromethyl ether. The purine base, B, is then conjugated to the resulting acyclic moiety by displacement of the chloride with purine, using, for example, a silated purine according to the method of Robins, M. J. et al, *Can J Chem* (1982) 60:547-553.

The resulting diester is, of course, a compound of the invention, that can be converted to the free acid by a modification of the method of McKenna, et al, *Tet Letts* (1977) 155.

The monoester is prepared by treatment of the diester with aqueous 1N sodium hydroxide, as described by Jones and Moffatt, *J Am Chem Soc* (1968) 90:5337. Any 6-chloro group on the purine will simultaneously be replaced by —OH.

The intermediate alcohol is obtained by methods which depend on the nature of R1 and R2. When R1 and R2 are either both methyl or both H, this alcohol is made according to Reaction Scheme 2.

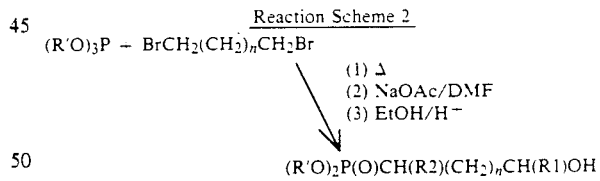

Reaction Scheme 2 describes the condensation of a trialkyl phosphite, wherein R' represents alkyl, with a symmetric dibromoalkane, according to the procedure of Eberhard and Westheimer, *J Am Chem Soc* (1965) 87:253.

However, when R2 is H and R1 is hydroxymethyl or methyl, the required alcohol intermediate is prepared according to Reaction Scheme 3.

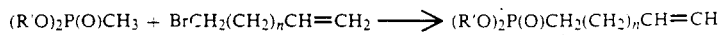

Reaction Scheme 3

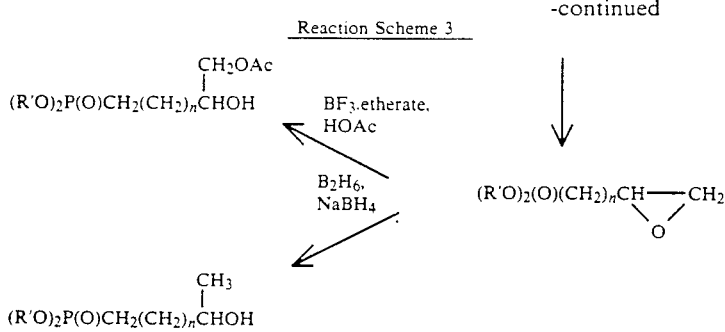

The initial condensation of Reaction Scheme 3 is according to the method of Savignac, et al., *Synth Comm* (1979) 9:487. Treatment of the resulting unsaturated butyl phosphonate with meta-peroxybenzoic acid, as shown, gives the epoxide. The epoxide can then be cleaved with $BF_3$ etherate in glacial acetic acid to obtain an acetoxymethyl intermediate for R1 as hydroxymethyl; or can be reduced with diborane and sodium borohydride to yield R1 as methyl.

For embodiments wherein R1 is H and R2 is OH, Reaction Scheme 4 is employed to form the intermediate alcohol, derivatized to the silyl ether.

Reaction Scheme 4

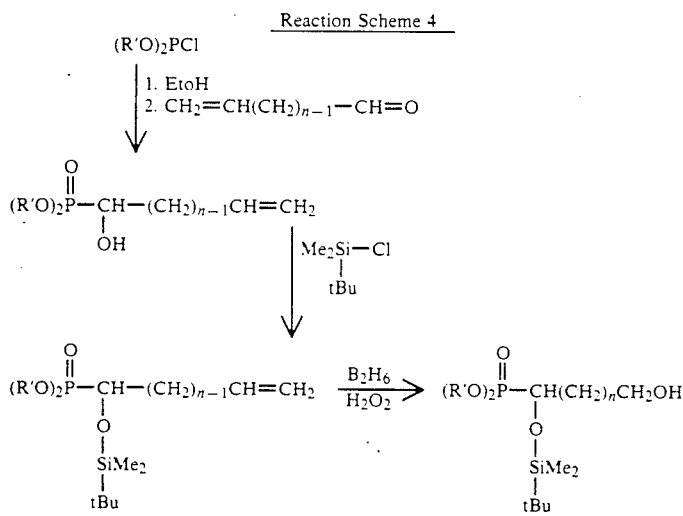

In this process, the intermediate phosphonate is prepared as described by Gazizov, T., et al, *J Gen Chem USSR* (1977) 47:2465, and then derivatized with alkyl chlorosilane before functionalization of the alkene to form the desired alcohol.

C. Interconversion of Salt and Ester Derivatives

The compounds of Formulas 1 and 1a may be prepared in their salt or ester forms, and these esters or salts can be reconverted to the free acid or free purine base.

Phosphonic Acid Salts

If desired, the free phosphonic acid may be converted to the mono- or dibasic salt form by treatment with an appropriate base. These salts are prepared by treating the corresponding free acids with at least one or at least two molar equivalents of a pharmaceutically acceptable base as set forth above. The reaction is conducted in water, alone or in combination with an inert, water-miscible organic solvent at a temperature of from 0° C.-100° C., preferably room temperature. Typical inert, water-miscible organic solvents include methanol, ethanol and dioxane. The stoichiometry of the resulting salt is dependent on the stoichiometry of the reaction components.

The salts can be reconverted to the phosphonic acid by standard procedures, e.g. by neutralizing with an acid resin or, less preferably, with an organic acid.

Acid Addition Salts

Alternatively, acid addition salts of the purine moiety may be prepared by reacting a compound of the invention with an acid such as the organic or inorganic acids exemplified above. The free base is dissolved in an polar organic solvent such as methanol or ethanol and the acid is added at a temperature of 0°-100° C., preferably at room temperature. The resulting salt either precipitates or may be brought out of solution by addition of a less polar solvent.

Conversely, the acid addition salt is reconverted to the free base by treating with suitable base.

Phosphonic Acid Esters

Desired esters of the phosphonic acid moiety may be prepared by transesterification of the phenyl esters using methods illustrated by Jones and Moffatt, *J Am Chem Soc* (1968) 90:5337. Although the examples below result in diethyl esters, the corresponding phenyl esters could be prepared by analogous methods by substituting phenyl phosphonate ester starting materials for the ethyl phosphonate ester starting materials illustrated.

The esters can be reconverted to the free acids by hydrogenolysis of the benzyl or hydrolysis of trimethyl silyl esters. These esters may be prepared by transesterification as above described.

Esters of R1/R2 Alcohols

These esters can result directly from the synthetic pathways illustrated below.

D. Utility and Administration

The compounds of this invention (including the physiologically acceptable salts and esters thereof) have antiviral activity against herpes virus forms and against RNA retroviruses. The compounds are conveniently formulated into pharmaceutical preparations composed of one or more of the compounds in association with a pharmaceutically acceptable carrier. *Remington's Pharmaceutical Sciences*, latest edition, by E. W. Martin (Mack Publ. Co., Easton, Pa.) discloses typical carriers and methods of preparation known in the art.

The compounds may be administered topically, orally, parenterally (e.g., intravenously), by intramuscular injection, or by intraperitoneal injection, or the like, depending upon the nature of the viral infection being treated. For internal infections the compositions are administered orally or parenterally at dose levels of about 0.1 to 300 mg/kg, preferably 1.0 to 30 mg/kg of mammal body weight and can be used in humans in a unit dosage form administered one to four times daily in the amount of 1–250 mg per unit dose.

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Alternatively, for topical infections, e.g., mouth and skin, the compositions are preferably applied to the infected part of the body of the patient topically as an ointment, cream, aerosol, or powder, preferably as an ointment or cream. The compounds may be presented in an ointment, for instance with a water soluble ointment base, or in a cream, for instance with an oil in water cream base in a concentration of from about 0.01 to 10%, preferably 0.1 to 7%, most preferably about 0.5% w/v. Additionally, viral infections of the eye, such as Herpetic keratitis, may be treated by use of a sustained release drug delivery system as is described in the art.

The exact regimen for administration of the compounds and compositions disclosed herein will necessarily be dependent upon the needs of the individual subject being treated, the type of treatment, and, of course, the judgement of the attending practitioner.

E. EXAMPLES

The invention will be further described by the following nonlimiting examples.

EXAMPLE 1

Preparation of 6-Chloro-9(3'-diethyl phosphono-1'-propyloxymethyl) Guanine

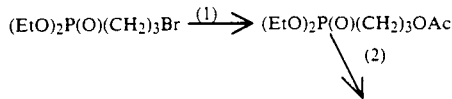

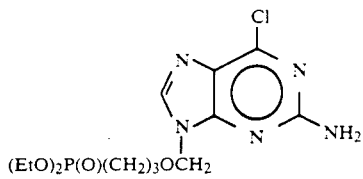

(This is not precisely a guanine derivative, since the —OH at position 6 is not present, and "B" should properly be called 2-amino-6-chloropurine; however, 6-chloroguanine is conventionally used.)

Diethyl-3-hydroxypropylphosphonate (steps 1 and 2) is prepared from diethyl-3-bromopropylphosphonate. Diethyl-3-bromopropylphosphonate (12.0 g, 46 mmol), prepared by the method of Eberhard, A., et al, *J Am Chem Soc* (1965) 87:253–260) was stirred with 12.0 g NaOAc.3H$_2$O in 125 ml DMF heated in a steam bath. The reaction was evaporated to dryness in vacuo after 2 hours and partitioned between H$_2$O and EtOAc, extracting the aqueous layer five times. The ethyl acetate extract was washed once with brine, dried with Na$_2$SO$_4$, filtered, and evaporated to dryness in vacuo to yield 9.8 g light yellow oil (89%). $^1$H NMR (CDCl$_3$) δ1.3 (tr, 6 H), 1.5–2.0 (m, 4 H), 2.03 (s, 3 H), 4.1 (dq, 6 H); thin-layer chromatography on SiGF developed with 2:1 EtOAc:CH$_2$Cl$_2$ gave R$_f$ 0.30. The isolated diethyl-3-acetoxypropylphosphonate (9.8 g, 41 mmol) in 200 ml abs. EtOH was stirred with 30 ml Dowex 50 (H$^+$) which had been rinsed three times each with H$_2$O and EtOH. After 4½ days at room temperature, another 10 ml of similarly prepared resin was added. Six hours later, the reaction was filtered and evaporated in vacuo. The quantitative yield of yellow oil was purified by dry column chromatography on 400 g silica packed in a 2.75-inch flat diameter nylon tube. The column was eluted with 1:9 MeOH:EtOAc and the appropriate fractions were cut and slurried with 1:1 MeOH:EtOAc. Filtration and evaporation in vacuo afforded 5.33 g (66%) pale yellow oil, which is the diethyl ester of 3-hydroxypropyl phosphonic acid. $^1$H NMR (CDCl$_3$, D$_2$O): δ1.3 (tr, 6 H), 1.6–2.08 (m, 4 H), 3.67 (tr, 2 H), 4.13 (dq, 4 H); thin-layer chromatography on SiGF developed with 1:9 MeOH:EtOAc gave an R$_f$ of 0.57.

Conversion to diethyl-3-chloromethoxypropyl phosphonate was according to the procedure of Kelley, J. L., et al, *J Med Chem* (1981) 24:1528–1531.

To 0.5 g (2.95 mmol) 2-amino-6-chloropurine, silated and treated with Hg(CN)$_2$ according to the procedure of Robins, M. J., et al, *Can J Chem* (1982) 60:547–553, in 40 ml benzene, was added a solution of 2.68 mmol diethyl-3-chloromethoxypropylphosphonate prepared as above. The reaction was refluxed for 2 hours, cooled, and 400 ml CHCl$_3$ was added. The organic phase was washed successively with 80 ml each of aqueous saturated NaHCO$_3$ and 1M aqueous KI. The organic solution was dried over Na$_2$SO$_4$, filtered, and evaporated to 790 mg of yellow gum. A portion of this crude material was used to conduct hydrolysis experiments. The remaining material was chromatographed on a silica column. A solution of 574 mg of the crude reaction product was placed on 20 g silica packed in a column using 5:3 EtOAc:nPrOH. Elution with the same mixed solvent afforded sixteen fractions of 10–20 ml each. Fractions 7-12 were combined to yield 258 mg of a colorless oil which spontaneously crystallized. Trituration in $CH_2Cl_2.Et_2O$ afforded two crops of white solid (207 mg), mp 109°-110° (28%). A yield of 46% of the diethyl ester was obtained from a reaction performed on 45.2 mmol of the starting purine. Anal $(C_{13}H_{21}ClN_5O_4P)$ C,H,N; UV $\lambda_{max}$ ($\epsilon$): pH 1, 246 ($\epsilon$6600), 310 (7200); pH 7, 247 (6800), 308 (7400); pH 11 247 (6600), 308 (7100); mass spectrum: m/e 377 (M+); $^1$H NMR (CDCl$_3$): $\delta$1.3 (tr, 6 H), 1.52-2.18 (m, 4 H), 3.58 (tr, 2 H), 4.09 (dq, 4 H), 5.48 (s. with broad base, 4 H), 7.89 (s, 1H). Thin-layer chromatography on SiGF developed with 5:3 EtOAc:nPrOH gave R$_f$0.40.

EXAMPLE 2

Preparation of 9(3'-ethylphosphono-1'-propyloxymethyl)guanine

A. 6-Chloro-9(3'-diethylphosphono-1'-propyloxymethyl) guanine (75 mg; 0.2 mmol) prepared as in Example 1 was combined with 5 ml 1N aqueous NaOH and refluxed 1 hour. The cooled reaction was neutralized with Dowex 50X8 (pyridinium form) and filtered, rinsing liberally with water. The solution was partially evaporated to remove pyridine and was then lyophilized. The orange-colored residue (74 mg) was redissolved in H$_2$O and centrifuged to remove insoluble material. The decanted solution (2 ml) was chromatographed on a 0.9×46 cm column of Whatman DE-52 Cellulose, HCO$_3$ form, using a linear gradient of one liter each H$_2$O and 0.2 M NH$_4$HCO$_3$ after an initial H$_2$O elution. Fractions (7 ml each) 43-47 yielded 25 mg (36%) of fluffy white solid after three lyophilizations. Electron impact mass spectrum (TMS derivative) showed m/e 547 (M+ of TMS derivative); chemical ionization mass spectrum (TMS derivative)showed m/e 548 (M+ +H of TMS$_3$ derivative). $^1$H NMR (D$_2$O) showed $\delta$1.19 (tr, 3 H), 1.4-1.9 (m, 4 H), 3.59 (tr, 2 H), 3.90 (dq, 2 H), 5.47 (s, 2 H), 8.2 (brs, 1 H). Thin-layer chromatography behavior on SiGF: R$_f$=0.40 when developed with 7:3 CH$_3$CN:0.1N aqueous NH$_4$Cl. Material obtained from passage through a column of Dowex 50X8 (H+) had a formula of $(C_{11}H_{18}N_5O_5P.H_2O)$ Calc: C-37.82% H-5.77%, N-20.05. Found: C-38.27%, H-5.84%, N-19.65%. A UV spectrum was run on the material and showed UV $\lambda_{max}$ ($\epsilon$): pH 1, 255 (11,900), 278 shoulder; pH 7, 252 (12,800) 271 shoulder; pH 11, 257 (10,700) 267 shoulder.

(The hydrolysis to the monoester simultaneously effects dehalogenation of the purine ring.)

B. In an improved procedure, a mixture of 6-chloro-9(3'-diethylphosphono-1'-propyloxymethyl) guanine (4.27 g, 11.3 mmol) and 1N aqueous NaOH (200 ml) was gently refluxed for 1 hour. The cooled reaction was neutralized and desalted with Dowex 50×8 (pyridinium form). The resin was removed by filtration, rinsing thoroughly with water. The aqueous filtrates were partially evaporated to remove pyridine and then lyophilized. A solution of the residue (3.68 g) in H$_2$O (30 ml, pH 8) was chromatographed on a bed of DEAE-Cellulose (Whatman DE 52, HCO$_3^-$ form, 2.5×100 cm). After an initial water wash to constant baseline, the column was eluted with a linear gradient of two liters each H$_2$O and 0.1N NH$_4$HCO$_3$. Fractions (20 ml each) 89-139 were combined and lyophilized to constant weight (2.25 g).

At 0° C., a solution of this material in a minimum amount of H$_2$O plus an equal amount of EtOH was treated with cold 1N HCl to pH 3.5 to yield 1.31 g (34%) of the title compound as a fine white solid. Electron impact mass spectrum (TMS derivative) showed m/e 547 (M+ of TMS$_3$ derivative); chemical ionization mass spectrum (TMS derivative) showed m/e 548 (M+ +H of TMS$_3$ derivative); chemical ionization mass spectrum on underivatized compound gave m/e 332 (M+ +H). Further characterization by $^1$H NMR (DMSO-d$_6$) showed $\delta$1.17 (tr, 3H), 1.3-1.8 (m, 4H), 3.48 (tr, 2H), 3.85 (dq, 2H), 5.3 (s, 2H), 6.46 (brS, 2H), 7.79 (s, 1H). An ultraviolet spectrum showed UV $\lambda_{max}$ ($\epsilon$): pH 1, 254 (12,800) 275 shoulder; pH 7, 252 (13,200) 272 shoulder; pH 11, 257 (11,400) 267 shoulder. The material had a formula of $(C_{11}H_{18}N_5O_5P.\frac{1}{2}H_2O)$. Calc: C-38.82%, H-5.63%, N-20.58%. Found: C-38.52%, H-5.90%, N-20.34%. Thin layer chromatography behavior on SiGF: R$_f$=0.40 when developed with 7:3 CH$_3$CN:0.1N NH$_4$Cl.

EXAMPLE 3

Conversion of the Monoester to Free Acid: 9(3'-Phosphono-1'-propyloxymethyl)guanine In a modification of the procedure of McKenna et al. Tet. Letters, (1977) 155, to a stirring mixture of 200 mg (0.57 mmol) 9(3'-ethylphosphono-1'-propyloxy methyl)guanine in CHCl$_3$ (8.3 ml) and hexamethyldisilazane (8.3 ml) at room temperature was added 0.61 ml (4.60 mmol) bromotrimethylsilane. After 72 hours, the mixture was evaporated to dryness, slurried with H$_2$O, and filtered, rinsing with acetone. A white solid (125 mg) was obtained. $^1$H NMR indicated no ethyl groups, and thin-layer chromatography on SiGF (7:3 CH$_3$CN: 0.1N NH$_4$Cl) revealed a single spot at Rf 0.20. The sodium salt was generated from Dowex 50×2 (Na+) to yield 114 mg (58%) white solid after lyophilization. $^1$H NMR (DMSO.d$_6$+D$_2$O) showed $\delta$1.68 (m, 4H), 3.60 (tr, 2H), 5.48 (s, 2H), 7.96 (s, 1H). An ultraviolet spectrum showed $\lambda_{max}$ ($\epsilon$): pH 1, 256 (10,800) 278 shoulder; pH 7, 256 (11,800) 270 shoulder; pH 11, 256 (10,200) 268 shoulder. Microanalysis afforded the formula $(C_9H_{13}N_5O_5P.Na.H_2O)$ Calc: C-31.49%, H-4.41%, N-20.41%, P-9.02%. Found: C-31.52%, H-4.55%, N-20.10%, P-8.21%; mass spectrum m/e 591 (M+ for TMS$_4$ derivative).

EXAMPLE 4

Preparation of 6-Chloro-9(7'-diethylphosphono-1'-heptoxymethyl)-guanine

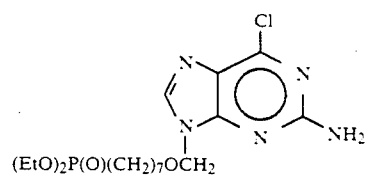

Diethyl7-chloromethoxyheptylphosphonate was prepared from 1,7-dibromoheptane and triethylphosphite in a manner analogous to that of Example 1. It was reacted with silated 2-amino-6-chloropurine, and mercuric cyanide as described for the preparation of 6-chloro-9(3-diethylphosphono-1-propyloxymethyl)guanine in Example 1 to give 32% of product as a colorless gum. UV $\lambda_{max}$ ($\epsilon$): pH 1-246 nm (6970), 310 nm (7190); pH 7-247 nm (6620), 310 nm (7180); pH 11-246 nm (6660), 309 nm (7140); $^1$H NMR (CDCl$_3$) $\delta$1.1-1.9 (m, 18 H), 3.48 (t, 2 H), 4.10 (dq, 4 H), 5.47 (s, 2 H), 5.88 (s, 2 H), 7.93 (s, 1 H). Thin-layer chromatography on SiGF gave $R_f 0.15$ using ethyl acetate:ethanol (100:1); analysis shows $C_{17}H_{29}ClN_5O_4P \cdot H_2O$.

EXAMPLE 5

Conversion to the Monoester: 9(7'-ethylphosphono-1'-heptyloxymethyl)guanine

6-Chloro-9(7'-diethylphosphono-1-heptyloxymethyl) guanine of Example 4 was hydrolyzed by refluxing 1N aqueous sodium hydroxide for 4 hours and isolated in 30% yield as described for the preparation of 9-(3'-ethyl phosphono-1'-propyloxymethyl)guanine (Example 2). It had $R_f 0.5$ on SiGF using acetonitrile:0.1N aqueous ammonium chloride, (7:3). Proton NMR ($D_2O$): $\delta = 1.1-1.5$ (m, 15 H), 3.5 (t, 2 H), 3.90 (dq, 2 H), 5.45 (s, 2 H). UV $\lambda_{max}$ ($\epsilon$): pH 7, 252 (12,200). Mass spectrum m/e 603 ($M^+$ for $TMS_3$ derivative).

EXAMPLE 6

Preparation of 9(3'-ethylphosphono-1'-hydroxymethyl-1'-propyloxymethyl)guanine

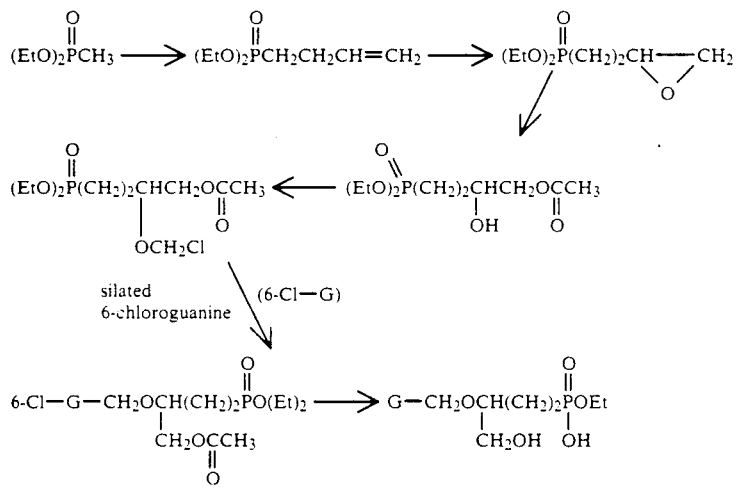

A. Preparation of Diethyl-3,4-epoxybutanephosphonate.

Diethyl-3,4-epoxybutanephosphonate was synthesized according to the procedure of Savignac et al., Syn Comm (1979) 7:487. In several syntheses, oxidation of the intermediate olefin compound produced a contaminating white solid which was removed by filtration of the crude, neat reaction product and rinsing the solid with ice cold $CH_2Cl_2$. Evaporation of the filtrate and distillation of the residue gave the epoxide in 75% yield.

B. Preparation of Diethyl 3-hydroxy-4-acetoxy butyl phosphonate

To a stirring solution of 2.51 g (12 mmol) diethyl-3,4-epoxybutanephosphonate in glacial acetic acid (10 ml) at room temperature in a dry, inert atmosphere was added 0.2 ml $BF_3$ etherate. After stirring 1 hour, $H_2O$ (20 ml) was added; the reaction was stirred 10 minutes and evaporated in vacuo. $H_2O$ was twice added and reevaporated to azeotrope HOAc. The residual syrup was partitioned between saturated aqueous $NaHCO_3$ (30 ml) and $Et_2O$ (20 ml). The aqueous phase was extracted with $CHCl_3$ (3×20 ml). The $CHCl_3$ extract was washed once with $H_2O$ (10 ml), dried ($Na_2SO_4$), filtered, and evaporated to obtain 2.15 g (67%) colorless oil. $^1H$ NMR ($CDCl_3 + D_2O$) spectral data indicated this material to be 85% pure as measured by the ratio of the —$OCOCH_3$ singlet at 2.1$\delta$ to the $(CH_3CH_2O)_2PO$— triplet at 1.32$\delta$. GC/MS data on the TMS derivative indicated one major component whose fragmentation pattern contained an extremely intense absorbance at m/e 267 with only small absorbance seen at m/e 237. This information is supportive of the structure for the desired isomer

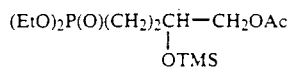

versus undesired

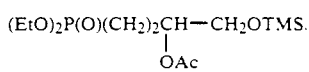

C. Preparation of 6-Chloro-9(3'-diethylphosphono-1'-acetoxymethyl-1'-propyloxymethyl)guanine.

6-Chloro-9(3'-diethylphosphono-1'-acetoxymethyl-1'-propyloxymethyl)guanine was prepared by coupling 112 mmol silated 6-chloroguanine with 108 mmol diethyl-3-chloromethoxy-4-acetoxybutylphosphonate ($^1H$ NMR: doublet at 5.54$\delta$ for —$OCH_2Cl$, prepared analogously to Example 1); according to the procedure of Example 1 for 6-chloro-9(3'-diethyl phosphono-1'-propyloxymethyl)guanine. The reactions remained at room temperature 1 week after a 3 hour reflux period. Due to the persistence of TMS groups after the usual workup procedure in earlier syntheses, EtOH (400 ml) was added to the reaction and stirred 1 hour before the workup was begun. The crude yellow gum obtained in 72% yield (34.9 g) was purified by flash chromatography on 330 g adsorbent (Baker silica for flash chromatography) by stepwise elution with 2.5, and 8% EtOH in $CHCl_3$. Combination of the appropriate fractions yielded 7.95 g (16%) 6-chloro-9(3'-diethylphosphono-1'-acetoxymethyl-1'-propyloxymethyl)guanine as a light yellow oil. Thin-layer chromatography on SiGF (9:1 $CH_2Cl_2 \cdot$ EtOH) showed a single spot at Rf 0.61. $^1H$ NMR ($CDCl_3 + D_2O$): $\delta 1.3$ (tr), 1.45–2.1 (m), 3.58 (d), 3.86–4.27 (m), 5.50 (assym d), 7.84 (d). Integration indicates that the aromatic to —OCH$_2$N— protons are present in a 1:2 ratio and that protons upfield of 5.5 δ (—OCH$_2$N—) are present in 80% excess. An ultraviolet spectrum showed λ$_{max}$ (EtOH) 248, 311; TOD$_{248}$ 14.4/mg; TOD$_{248}$ 16.9/mg for 6-chloro-9(3′-diethylphosphono-1′-propyloxymethyl)guanine from Example 1.

D. Conversion to the Monoester and Hydrolysis: 9(3′-ethylphosphono-1′-hydroxymethyl-1′-propyloxymethyl)guanine The hydrolysis of 7.95 g (17.7 mmol) 6-chloro-9(3′-diethylphosphono-1′-acetoxymethyl-1′-propyloxymethyl)guanine with 1N aqueous NaOH (130 ml) was conducted as in Example 3B for the synthesis of 9(3′-ethyl phosphono-1′-propyloxymethyl)guanine. Material isolated from DEAE-Sephadex (2.5×97 cm A-25, HCO$_3$⁻) chromatography required purification on a second similar column again using a linear gradient of H$_2$O and 0.1N NH$_4$HCO$_3$ (2.0 liters each). Examination of fractions by HPLC (Vydac TP21854, 1% CH$_3$CN in 0.0125N triethylammonium formate, pH 3, 2 ml/min, 252λ), of ultraviolet spectra and of the total optical density (TOD$_{252}$$^{pH7}$) relative to the weight obtained after several lyophilizations allowed one to obtain two pure fractions of 9(3′-ethylphosphono-1′-hydroxymethyl-1′-propyloxymethyl)guanine (1.0 g each, 29%, 36 TOD$_{252}$$^{pH7}$/mg), one of which contained an isomer ratio of 3:2 by HPLC and the second, an isomer ratio of 1:1. Microanalysis of the latter sample gave the formula (C$_{12}$H$_{20}$N$_5$O$_6$P.$\frac{1}{4}$ NH$_3$.1 H$_2$O). Calc: C-37.57%, H-5.98%, N-19.17%. Found: C-37.47%, H-5.50%, N-19.16%. UV λ$_{max}$ (ε): pH 1, 256 (12,400) 276 shoulder; pH 7, 252 (13,500) 270 shoulder; pH 11, 256 (11,800) 266 shoulder. $^1$H NMR (D$_2$O): δ1.22 (d tr, 3H), 1.35–1.88 (m, 4H), 3.48–4.0 (m, 5H), 5.52 (d, 2H), ~7.9 (very broad singlet, 1H). Thin-layer chromatography on SiGF: Rf 0.32 (7:3 CH$_3$CN:0.1N NH$_4$Cl).

EXAMPLE 7

Preparation of 9(3′-Phosphono-1′-hydroxymethyl-1′-propyloxymethyl)guanine

9(3′-Ethyl phosphono-1′-hydroxymethyl-1′-propyloxymethyl)guanine (204 mg, 0.52 mmol of the partial ammonium salt) was treated with bromotrimethylsilane (0.8 ml, 6.13 mmol) in a procedure similar to the synthesis of 9(3′-phosphono-1′-propyloxymethyl)guanine of Example 4. To aid in solubilization of the starting material in the reaction medium, 1,5-diazabicyclo[5.4.0]undec-5-ene (0.078 ml, 0.52 mmol) was added. After stirring overnight at room temperature, the mixture was evaporated to dryness. The residue was dissolved readily in 3 ml H$_2$O and was treated with several drops of 1M HCl to acidity and reevaporated. Trituration with EtOH followed by filtration yielded 161 mg off-white solid (93%). Thin-layer chromatography on SiGF (7:1:2, iPrOH:NH$_4$OH:H$_2$O) gave Rf 0.18. UV λ$_{max}$: pH 1, 256, 278 shoulder; pH 7, 252, 272 shoulder; pH 11, 255, 268 shoulder. $^1$H NMR (D$_2$O) C: 1.55–1.85 (m, 4H), 3.5–3.95 (m, 3H), 5.58 (d), 7.95 (brS, 1H). Mass spectrum m/e 693 (M⁻ for TMS$_5$ derivative).

EXAMPLE 8

Preparation of 9(3′-phosphono-1′-hydroxymethyl-1′-propyloxymethyl)guanine cyclic ester In a procedure similar to that of Khorana, H. G., et al in *J Am Chem Soc* (1961) 82:698, a mixture of 0.011 g (0.033 mmol) 9(3′-phosphono-1′-hydroxymethyl-1′-propyloxymethyl)guanine (Example 9) in 6 ml dry pyridine was treated with 0.010 g (0.034 mmol) N′,N′-dicyclohexyl-4-morpholine carboxamidine at reflux. After solution was complete, a hot solution of 0.012 g (0.058 mmol) dicyclohexylcarbodiimide in 4 ml pyridine was added in a single portion, and the solution was heated at gentle reflux for 2$\frac{1}{2}$ hours. The reaction was evaporated to dryness. The residue was triturated in H$_2$O and filtered. The filtrate was evaporated to dryness, then solubilized in MeOH. Thin-layer chromatography on SiGF showed a single spot at R$_f$=0.70 using iPrOH:NH$_4$OH:-H$_2$O (7:1:2) R$_f$=0.41 using CH$_3$CN:0.01N NH$_4$Cl (7:3), and R$_f$=0.78 using MeOH. UV λ$_{max}$: pH 7, 251, 275 shoulder. Mass spectrum m/e 531 (M⁻ for TMS$_3$ derivative).

EXAMPLE 9

Preparation of 8-Bromo-9(3′ethylphosphono-1′-propyloxymethyl)guanine

A stirring mixture of 97 mg (0.286 mmol) 9(3′-ethylphosphono-1′-propyloxymethyl)guanine prepared in Example 2 in H$_2$O (5 ml) was treated with a saturated Br$_2$ in H$_2$O solution according to the procedure of Robins, M. J., et al., *J Med Chem* (1984) 27:1486–1492 until the bromine color persisted (3–4 ml). After stirring 30 minutes at room temperature, the color was discharged with crystals of NaHSO$_3$. The reaction was filtered, then washed with H$_2$O and EtOH, to collect 99 mg (87%) white solid which appeared to be homogenous by thin layer chromatography using SiGF: R$_f$=0.33 using CH$_3$CN:0.1N NH$_4$Cl (7:3). $^1$H NMR (DMSO-d$_6$): δ1.19 (tr, 3H), 1.3–1.9 (m, 4H), 3.53 (tr, 2H), 3.92 (dq, 2H), 5.33 (S, 2H), 6.68 (brS, 2H). UV λmax (ε): pH 1, 260 (16,400); pH 7, 260 (16,400), pH 11, 269 (13,600).

HPLC examination of the compound on a Vydac TP-21854 column (4.6×250 mm) with a 15 min non-linear gradient of 0 to 100% 'B' in 'A', where 'A' is 0.0125N Et$_3$N.HCO$_2$H, pH 3.0 and 'B' is 5% aqueous CH$_3$CN (program #8 on Waters Model 660 solvent programmer) indicated about 5% starting material. Chromatography on DEAE sephadex as related in Example 1 using a linear gradient of water and 0.1N NH$_4$HCO$_3$ yielded product title compound free of starting material.

17

EXAMPLE 10

Preparation of
9(3'-Ethylphosphono-3'-hydroxy-1'-propyloxymethyl)-
guanine

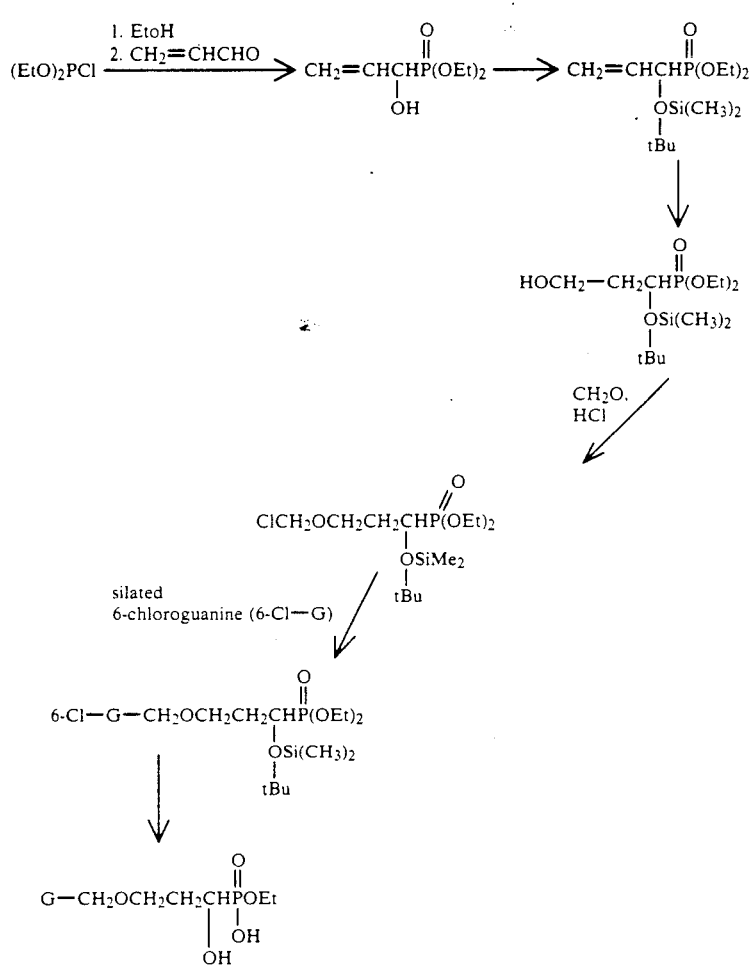

A. Preparation of Diethyl 1-t-butyldimethylsilyloxy allyl phosphonate

A solution of 68.8 g (0.355 mole) diethyl 1-hydroxyallyl phosphonate, prepared as reported by Gazizov, et al, *J Gen Chem USSR* (1977) 47:2465, (Eng. Trans., p. 2253), in 120 ml dry DMF was combined with 60.44 g (0.888 mole) imidazole and treated with 63.87 g (0.424 mole) t-butyldimethylchlorosilane according to the procedure of Corey, E. J., et al, in *J Am Chem Soc* (1972) 94:6190. The reaction was stirred at room temperature for 24 hours and combined with 750 ml Et$_2$O. The biphasic solution was washed with H$_2$O (3×250 ml). The organic layer was dried with MgSO$_4$, gravity filtered, and evaporated to dryness for a quantitative yield (110 g) of a colorless oil. Thin-layer chromatography showed a spot on SiGF (10% EtOAc in CHCl$_3$-visualization with 2% phosphomolybdic acid plus heat) at Rf 0.44 with trace impurity at Rf 0.61. $^1$H NMR (CDCl$_3$): δ0.10 and 0.13 (s, s, 5H), 0.97 (s, 9H), 1.33 (tr, 6H), 4.2 (dq, 4H), 457 (dd, 1H), 5.1–5.63 (m, 2H), 5.87–6.34 (m, 1H).

18

B. Preparation of Diethyl 1-t-butyldimethylsilyloxy-3-hydroxypropyl phosphate Diethyl 1-t-butyldimethylsilyloxyallyl phosphonate (76 g, 0.247 mole) was azeotroped from toluene three times and dissolved in 400 ml dry THF. 1M diborane in THF (150 ml) was added dropwise at 25° C. over 45 minutes and the reaction then stirred an additional 1 hour. The hydroboration was terminated by addition of 65 ml H$_2$O maintaining the temperature at 20° C. with ice cooling. 3N NaOH (20 ml) was added followed by dropwise addition of 80 ml 30% H$_2$O$_2$ with ice cooling to keep temperature at 40° C. The pH was checked intermittently and, when no longer alkaline, another 20 ml plus 10 ml 3N NaOH was added in 2 portions. After addition of H$_2$O$_2$, the reaction was maintained at 35° C. for an additional 20 minutes. EtOH (40 ml) was added to improve miscibility. The reaction was poured into 800 ml Et$_2$O; 300 ml H$_2$O plus 25 ml solid NaCl was added, stirred well, and placed in the refrigerator overnight. The layers were separated and the Et$_2$O layer was washed thoroughly with H$_2$O saturated with NaCl to minimize emulsions. The Et$_2$O solution was dried with MgSO$_4$, filtered, and evaporated to yield 70.25 g (87%) yellow oil. Thin-layer chromatography on SiGF (EtOAc, 5% phosphomolybdic acid plus heat) showed two spots at Rf 0.35 and 0.55 in approximately 2:3 ratio. In a previous synthesis, the material at Rf 0.55 was identified as the secondary alcohol and the material at Rf 0.35 as the primary alcohol. $^1$H NMR (CDCl$_3$)

$\delta$ 0.083 and 0.113 (s, s, 3H, 3H, —Si(CH$_3$)$_2$), 0.882 (s, 9H, SiC(CH$_3$)$_3$), 1.314 and 1.317 (tr, tr, 6H, —P-(OCH$_2$CH$_3$)$_2$), 1.9-2.1 (m, 2H, HOCH$_2$CH$_2$—), 3.69 and 3.87 (ddq, dq, 2H, HOCH$_2$—), 4.07-4.22 (m, 5H, —POCH$_2$CH$_3$ and —CHPO—). In order to enhance chromatographic separation of the two alcohols, the crude material was tritylated according to the procedure of Chaudhary et al, *Tet. Letters* (1979) 95. The mixture of tritylated alcohols were separated on silica eluting with increments of CH$_2$Cl$_2$, 10%, 30%, and 50% EtOAc in CH$_2$Cl$_2$, and finally EtOAc. TLC on SiGF (10% EtoAc in CH$_2$Cl$_2$) of the tritylated primary alcohol showed R$_f$ 0.6. The trityl group was removed instantaneously at 0° C. with 1% HCl in CHCl$_3$ according to the procedure of Choy and Unrau, *Carbohydrate Res.* (1971) 17:439. Silica chromatography eluting with CH$_2$Cl$_2$, 10% EtOAc in CH$_2$Cl$_2$, and EtOAc provided 6.6 g of diethyl 1-t-butyldimethylsilyloxy-3-hydroxypropyl phosphonate.

C. Preparation of 6-Chloro-9(3'-diethyl phosphono-3'-t-butyldimethylsilyloxy-1'-propyloxymethyl)guanine The coupling of (0.020 mole) diethyl 1-t-butyldimethylsilyloxy-3-chloromethoxypropyl phosphonate and 6-chloroguanine was conducted according to the procedure set forth for 6-chloro-9(3'-diethyl phosphono-1'-propyloxy methyl)guanine in Example 1. Silica chromatography eluting with 10:1 EtOAc:iPrOH afforded 2.5 g (26%) white solid, Rf 0.79, mp 120°-123° C. $^1$H NMR (CDCl$_3$) $\delta$ 0.03 and 0.14 (s, s, 6H), 0.91 (s, 9H), 1.35 and 1.38 (tr, tr, 6H), 1.77-2.32 (m, 2H), 3.64 (tr, 2H), 3.88-4.27 (m, 5H), 5.24 (br s, 2H), 5.45 (s, 2H), 7.94 (s, 1H).

D. Preparation of 6-Chloro-9(3'-diethylphosphono-3'-hydroxy-1'-propyloxymethyl)guanine The t-butyldimethylsilyl group was removed from 1.62 g (3.4 mmol) 6-chloro-9(3-diethylphosphono-3'-t-butyldimethylsilyloxy-1'-propyloxymethyl)guanine in 30 ml dry THF by addition of 3.75 ml 1M tetrabutylammonium fluoride at 5° C. After stirring 22 minutes at 5° C., the reaction was evaporated to dryness and chromatographed in silica eluting with 1:1 EtOAc:iPrOH. 6-Chloro-9(3'-diethylphosphono-3'-hydroxy-1'-propyloxymethyl)guanine was obtained by evaporation of the appropriate fractions and crystallization from EtOAc to yield 0.95 g (71%) white solid, mp 116°-118° C. Thin-layer chromatography on SiGF (10:1 EtOAc . iPrOH) showed R$_f$ 0.21. Microanalysis confirmed the formula (C$_{13}$H$_{21}$ClN$_5$O$_5$P). Calc: C-39.65%, H-5.38%, N-17.79%. Found: C-39.59%, H-5.54%, N-17.32%. $^1$H NMR (CDCl$_3$): $\delta$ 1.31 (tr), 1.82-2.15 (m), 3.65-3.85 (m), 3.92-4.42 (m), 5.46 (s), 5.59 (brs), 7.85 (s). UV $\lambda_{max}$: 245, 306.

E. Conversion to Monoester and Dehalogenation

The hydrolysis of 0.645 g (1.64 mmol) of 6-chloro-9(3'-diethyl phosphono-3'-hydroxy-1'-propyloxymethyl)guanine with 32.5 ml 1N NaOH was conducted as set forth in Example 3 for the synthesis of 9(3'-ethyl phosphono-1'-propyloxymethyl)guanine. DEAE-Sephadex chromatography yielded 35 mg (6%) material with R$_f$ 0.48 on SiGF (7:3 CH$_3$CN: 0.1N NH$_4$Cl). $^1$H NMR (D$_2$O): $\delta$ 1.31 (tr), 1.72-2.20 (m), 3.76-4.1 (m), 5.68 (s). UV $\lambda_{max}$: pH 1 256, 278 shoulder; pH 7 251, 270 shoulder; pH 11 255, 265 shoulder. Mass spectrum m/e 635 (M$^+$ for TMS$_1$ derivative).

EXAMPLE 11

Using the procedures described above, the following compounds of the invention were prepared.

TABLE 1

| Compound # | B | R1 | R2 | n | Form |
|---|---|---|---|---|---|
| 1 | G | H | H | 1 | phosphonic acid |
| 2 | G | H | H | 1 | monoethylester |
| 3 | G | H | H | 1 | diethyl ester |
| 4 | G | H | H | 1 | monoethyl ester, monosodium salt |
| 5 | G | CH$_2$OH | H | 1 | monoethyl ester |
| 6 | G | CH$_2$OH | H | 1 | phosphonic acid |
| 7 | G | CH$_3$ | H | 1 | monoethyl ester |
| 8 | G | H | H | 5 | monoethyl ester |
| 9 | G | CH$_2$OH cyclic structure | H | 1a | phosphonic acid |
| 10 | * | H | H | 1 | diethyl ester |
| 11 | * | H | H | 5 | diethyl ester |
| 12 | ** | H | H | 1 | monoethyl ester |
| 13 | *** | H | H | 1 | monoethyl ester |
| 14 | G | H | OH | 1 | monoethyl ester |
| 15 | * | CH$_2$OH | H | 1 | diethyl ester (acetoxy ester) |
| 16 | * | H | OH | 1 | diethyl ester |

*6-chloroguanine(6-chloro-2-aminopurine).
**8-bromoguanine.
***2-NH$_2$-adenine (2,6-diaminopurine).

F. Biological Testing

The compounds of the invention were evaluated in vitro as antiviral agents against herpes virus and against RNA retrovirus. Various herpes strains were used. An infected B lymphoblastoid cell line was used as HIV substrate to test antiviral activity with respect to RNA retrovirus.

ACTIVITY AGAINST HERPES-TYPE VIRUS

One herpes virus strain employed was Strain McCrae of type 1 herpes (thymidine kinase positive virus) (HSV-1TK$^+$). This strain was prepared and titered in MA-104 cells and frozen at $-90°$ C. until use. Also used were strain HF (HSV-1TK$^-$). Strain E194 (HSV-2). NJB strain (MCMV), strain AD169 (HCMV).

Continuous passaged monkey kidney (MA-104) cells were used for testing of herpes-type virus, with growth medium consisting of Minimum Essential Medium (MEM) supplemented with 0.1% NaHCO$_3$ and 50 $\mu$l gentamicin.

To a 96 well microtiter plate containing an established 24 hour monolayer of cells from which the medium has been decanted was added 0.1 ml of varying (one-half log$_{10}$) concentrations of test compound, which incubated on the cell 15 minutes, after which 0.1 ml of virus in a concentration of 320 cell culture 50% infectious doses (CCID$_{50}$)/0.1 ml was added. The plate was covered with plastic wrap and incubated at 37° C. Included with the test were toxicity controls (each concentration of compound+test medium in place of virus), virus controls (virus+test medium in place of compound) and cell controls (test medium in place of compound and virus). The cells were examined microscopically after 72 hours for evidence of cytotoxicity and for viral cytopathic effect (CPE). Vidarabine was run on the same plate in parallel. The test compounds were added to the medium at a concentration of 2000 $\mu$g/ml for use as a positive control.

Antiviral activity was determined by observation of inhibition of viral CPE. This activity was expressed by $ED_{50}$, defined as that dose range of compound causing 50% CPE inhibition.

A Virus Rating (VR) was also determined. VR is a numerical expression of antiviral activity, weighted to take into account any cytotoxicity observed, as discussed by Sidewell et al, *Appl Microbiol* (1971) 22:797. Generally, a VR of 0.1–0.4 indicates slight antiviral effect, 0.5–0.9 indicates moderate antiviral effect, and ≧1.0 indicates strong antiviral effect.

The results of the foregoing assays are as follows: The activities of compounds 1 and 2, (9-(3'-phosphono-1'-propoxymethyl)guanine and its monoethyl ester), against HSV-1TK+ were comparable to that of vidarabine, as shown in Tables 2 and 3.

TABLE 2

| Anti HSV-1TK+ Activity | | | |
|---|---|---|---|
| Compound 1 | | Vidarabine | |
| Conc. (μg/ml) | CPE Inhib. (%) | Conc. (μg/ml) | CPE Inhib. (%) |
| 1000 | 100 | 1000 | 100 |
| 320 | 94 | 320 | 100 |
| 100 | 79 | 100 | 87 |
| 32 | 62 | 32 | 87 |
| 10 | 49 | 10 | 69 |
| 3.2 | 28 | 3.2 | 28 |
| 1.0 | 31 | 1.0 | 56 |
| VR | 1.4 | | 1.3 |
| $ED_{50}$ | 10 μg/ml | | 10 μg/ml |

An additional test of Compound 1 gave VR against HSV-1TK+ of 0.6; this compound was not active against murine CMV.

TABLE 3

| Anti HSV-1TK+ Activity | | | | | |
|---|---|---|---|---|---|
| Compound 2 | | | Vidarabine | | |
| Conc. (μg/ml) | Test 1 CPE Inhib. (%) | Test 2 CPE Inhib. (%) | Conc. (μg/ml) | Test 1 CPE Inhib. (%) | Test 2 CPE Inhib. (%) |
| 1000 | 100 | 76 | 1000 | 100 | 100 |
| 320 | 82 | 67 | 320 | 100 | 100 |
| 100 | 47 | 57 | 100 | 96 | 85 |
| 32 | 6 | 57 | 32 | 96 | 57 |
| 10 | 38 | 48 | 10 | 60 | 39 |
| 3.2 | 96 | 52 | 3.2 | 2 | 0 |
| 1.2 | 69 | 48 | 1.0 | 0 | 0 |
| VR | >2.0 | >1.4 | | 0.8 | 0.7 |
| $ED_{50}$ | <1.0 μg/ml | <1.0 μg/ml | | 10 μg/ml | 10 μg/ml |
| MTD* | 320 | >1000 | | 10 | 10 |

*Maximum tolerated dose, μg/ml.

Additional tests of Compound 2 against HSV-1TK− showed VR values of 0.4, 0.6, 0.9, 0.4, 0.3, and 0.7. Compound 2 was active against murine CMV (VR=0.6, 1.6, 2.3) and human CMV ($ED_{50}$=10 μg/ml).

Compound 5 (9-(3'-phosphono-1'-hydroxymethylpropoxymethyl) guanine, monoethyl ester, showed an $ED_{50}$ of 0.1–3.2 μg/ml against human CMV. It was mildly effective against HSV1TK+ and HSV-2.

Compound 2 also was tested in vivo in guinea pigs as an agent against HSV-1TK+. The animals were inoculated with the virus; 18 hours later Compound 2 at two concentrations (0.4% and 1-2% (saturated) solution in water) was administered, and five days later blister diameters at the point of inoculation were measured. A 5% solution of acyclovir or a 1.4% solution of poly(vinylalcohol) was used as control. Satellite lesions were measured, as well.

The results of these tests are given as average number of lesions in Table 4 and show that Compound 2 has activity against HSV TK− virus, at least in saturated solution.

TABLE 4

| Virus | Placebo poly (Vinylalcohol) | Acyclovir | Compound 2 1-2% | Compound 2 0.4% |
|---|---|---|---|---|
| TK− | 1.7 | 1.0 | 0.9 | 2.1 |
| Satellite lesions | 9 | 4 | 6 | 11 |

Table 5 shows the results of two experiments showing the antiviral activity of compounds 2 and 5 against human cytomegalovirus.

TABLE 5

| Compound Concentration (μg/ml) | Compound 2 | | Compound 5 | | Acyclovir | |
|---|---|---|---|---|---|---|
| | No. Plaques | % Reduct. | No. Plaques | % Reduct. | No. Plaques | % Reduct. |
| Experiment No. 1 | | | | | | |
| 100 | 0 | 100 | 1 | 94 | 1 | 94 |
| 32 | 5 | 71 | 2 | 88 | 7 | 59 |
| 0 | 17 | — | 17 | — | 17 | — |
| Approx. ED50$^a$ (μg/ml): | 10 | | 0.1 | | 10-32 | |
| Experiment No. 2 | | | | | | |
| 100 | 1 | 96 | 0 | 100 | 1 | 96 |
| 32 | 6 | 73 | 3 | 86 | 8 | 64 |
| 10 | 17 | 23 | 7 | 68 | 20 | 9 |
| 0 | 22 | — | 22 | — | 22 | — |

TABLE 5-continued

| Compound | Compound 2 | | Compound 5 | | Acyclovir | |
|---|---|---|---|---|---|---|
| Concentration (μg/ml) | No. Plaques | % Reduct. | No. Plaques | % Reduct. | No. Plaques | % Reduct. |
| Approx. ED50 (μg/ml)[a]: | 10-32 | | 3.2 | | 10-32 | |
| Approx. MTD[b]: | 1000 | | 1000 | | 1000 | |

[a]50% effective dose, determined from plot of data.
[b]Maximum tolerated dose: That dose causing approximately 50% cytotoxic effects in cells, determined by the microscopic examination of cells for sloughing, shape alteration, and granularity in separately run control tests in 96-well microplates.

The data on acyclovir were gathered from tests run in MRC-5 cells grown under agarose overlay, with plaques read 7 days after virus exposure. Overall, the data in Table 5 show that compound 1 and acyclovir appear to have approximately the same human CMV-inhibitory effects and cytotoxicity. Compound 5 appears to have a more potent anti-CMV effect than acyclovir, and to be no more cytotoxic.

ACTIVITY AGAINST RNA RETROVIRUS

The ability of compounds of the invention to exhibit antiviral activity against RNA retroviruses was shown in an in vitro assay similar to that described above and was also demonstrated by their ability to inhibit reverse transcriptase.

For the reverse transcriptase assay, cloned reverse transcriptase (RT) (Bethesda Research Laboratories) from Moloney murine leukemia virus (MMLV) or avian myeloblastosis virus (AMV) (Seikagaku or Boehringer Mannheim) was used to direct DNA synthesis from a polyribonucleotide template and a oligodeoxynucleotide primer under reaction conditions (Houts, G. E., et al, *J Virol* (1979) 29:517.)

Reaction mixtures (100 μl) for the assay of MMLV RT consisted of 50 mM Tris-hydrochloride, pH 8.0, 6 mM $MgCl_2$, 40 mM KCl, 100 μg bovine serum albumin per ml, 1 mM dithiothreitol, 0.1 mM polyadenylic acid (Pharmacia, Inc.), 0.1 mM oligo(dT)$_{12-18}$ (Pharmacia, Inc.), 0.4 mM deoxythymidine triphosphate (dTTP), and 0.1 mM tritiated (93.5 Cl/mmol) dTTP (New England Nuclear). The compounds assayed were added in various concentrations and dilutions at a volume of 10 μl. Results were confirmed by duplicate assays. Dilutions were made using 10% aqueous DMSO. The total activity was measured by spotting on dry Whatman 3 mm filter disks and radioactivity was determined by liquid scintillation techniques. The assay time course was begun by adding 10 units of RT from MMLV or AMV and incubating the reaction at 37° C. Aliquots (10 μl) were removed as a function of time and quenched in 20 μl of stop mix [0.25 mM EDTA, 0.5 mg/ml yeast tRNA (BDH Biochemicals, England), 10 mM sodium pyrophosphate]. The 30 μl samples were spotted onto Whatman 3 mm disks and batch-washed (10 ml/disk) in ice-cold 10% TCA, 1% sodium pyrophosphate for 10 minutes with agitation. This was followed by three 4 minute ice-cold 5% TCA batch washes and a final 95% ethanol rinse (1 minute). Disks were dried under a heat lamp and the acid-insoluble product radioactivity was determined by liquid scintillation counting. Blank assays were conducted using 10% DMSO. Phosphonoformic acid, trisodium salt (Sigma Chemical Company), dissolved in water was used as a positive control at a final concentration of 1 mM.

To test antiviral activity versus HIV, the following procedure was used: Infectious HIV was assayed in cell culture as described originally by Barre-Sinoussi et al for isolation of LAV, except that persistently infected lymphoblastoid cells were used instead of mononuclear cells from anti-LAV negative donors. HIV obtained from cell culture was stored in liquid nitrogen in aliquots of RPMI 1640 culture medium with 20% of total calf serum and 20% glycerol and containing 1,000 TCID-50 HIV. The lymphoblastoid cells ($10^6$) were incubated with 1,000 TCID-50 of HIV obtained from cell cultures, and cells were then cultured in RPMI-1640 medium. Culture medium was changed every 3 days for 3 weeks and the medium for each 3-day period from Day 6 through Day 21 was assayed for viral reverse transcriptase activity by concentrating (pelleting) virus by ultracentrifugation in the 100 place Spinco 25 rotor and assaying pellets for reverse transcriptase (RT) using a $^{32}$P-dTTP in the presence of dimer-template poly rA-oligo dT. Compounds to be tested for neutralization of infection were incubated with HIV aliquots ($10^3$ TCID-50) for 30 minutes at 22° C. before incubation with $10^6$ lymphoblastoid cells.

The results obtained in the foregoing assays were as follows: Compound 1, 9-(3-phosphono-1-propoxymethyl)guanine, showed 75% inhibition of reverse transcriptase at 8 mM concentration; compound 2, the monoethyl ester form, showed 100% inhibition at 1 mM. These activities were further reflected in $ED_{50}$ values against HIV, which were 40-50 μg/ml and 30 μg/ml, respectively.

G. Formulations

The following formulations based on the compounds of the invention and their preparation are representative.

A formulation suitable for injection intramuscularly or intraperitoneally is prepared by combining the first four of the following materials:

| Compound of the invention | 1 g |
|---|---|
| Poly (ethylene glycol) | 50 g |
| Propylene glycol | 50 g |
| Tween-80 suspension agent | 1.5 g |
| Injectable saline | 200 ml | and then adding the last material. The material forms a clear solution which is filtered and sealed in sterile containers.

A simple intravenous injection formulation is formed by dissolving 1 gram of an active compound in 250 ml of injectable saline which after filtering is packaged in sterile bottles.

A cream for topical administration is formulated by stirring 10 g of active compound of the invention with 20 g of mineral oil, 40 g of petroleum jelly, 0.3 g of mixed methyl/propyl paraben, and 5 g of nonionic surfactant at 50° C. Then 150 ml of water are stirred into the mixture at 50° C. at high speed to form a cream, and the mixture is cooled and packaged in capped tubes.

An oral dosage form is prepared from 10 g of a compound of the invention, 100 g of lactose, and 1 g of starch, which are mixed with 0.1 g of magnesium stearate in methanol to granulate. The methanol is removed by gentle heating with stirring. A portion of this material is retained as a granular powder for oral use while the remainder is hand formed into 250 mg tablets in a manual tableting machine.

The foregoing examples and formulations have been presented to illustrate the present invention and are not to be construed as limitations on the invention's scope, which is instead defined by the following claims.

What is claimed is:

1. The compound which is 9(3'-phosphono-1'-propyloxymethyl) guanine.
2. The compound which is 9(3'-ethylphosphono-1'-propyloxymethyl) guanine, monosodium salt.
3. The compound which is 9(3'-ethylphosphono-1'-hydroxymethyl-1'-propyloxymethyl) guanine.
4. The compound which is 9(7'-ethylphosphono-1'-heptyloxymethyl) guanine.
5. The compound which is 9(3'-phosphono-1'-hydroxymethyl-1'-propyloxymethyl)guanine.

* * * * *